United States Patent [19]

Urso

[11] Patent Number: 5,323,796
[45] Date of Patent: Jun. 28, 1994

[54] AUTOMATED DENTAL FLOSSER

[75] Inventor: Charles L. Urso, Waltham, Mass.

[73] Assignee: DynaProducts, Inc., Nashua, N.H.

[21] Appl. No.: 950,935

[22] Filed: Sep. 24, 1992

[51] Int. Cl.⁵ ............................................. A61C 15/00
[52] U.S. Cl. ..................................... 132/322; 433/119
[58] Field of Search ................... 433/118, 119; 132/322

[56] References Cited

U.S. PATENT DOCUMENTS

| | | | |
|---|---|---|---|
| 3,421,524 | 1/1969 | Waters | 132/322 |
| 3,667,483 | 6/1972 | McCabe . | |
| 3,759,274 | 9/1973 | Warner . | |
| 3,847,167 | 11/1974 | Brien . | |
| 4,245,658 | 1/1981 | Lecouturier . | |
| 4,281,987 | 8/1981 | Kleesattel | 433/119 X |
| 4,307,740 | 12/1981 | Florindez . | |
| 4,326,549 | 4/1982 | Hinding . | |
| 4,458,702 | 7/1984 | Grollimund . | |
| 4,605,025 | 8/1986 | McSpadden | 132/322 |
| 4,706,659 | 11/1987 | Urso . | |
| 4,880,382 | 11/1989 | Moret et al. | 433/118 |
| 5,000,884 | 3/1991 | Odrich | 433/118 X |
| 5,016,660 | 5/1991 | Boggs | 132/322 |
| 5,059,122 | 10/1991 | Hetzel | 433/119 X |
| 5,138,733 | 8/1992 | Boch | 433/119 X |
| 5,176,157 | 1/1993 | Mazza | 132/322 |

FOREIGN PATENT DOCUMENTS 9011057  10/1990  World Int. Prop. O. .......... 132/322

*Primary Examiner*—Gene Mancene
*Assistant Examiner*—Nicholas D. Lucchesi
*Attorney, Agent, or Firm*—Hamilton, Brook, Smith & Reynolds

[57] ABSTRACT

An automated dental flosser (10) comprises a pair of pivotally supported tines (18) which support a movable floss span (17). A pair of rotatably supported subcapstans (38, 40) are floss-connected to each end of the floss span, respectively, and are alternately driven to reciprocate the span longitudinally. A floss dispensing spool (50) and a floss take-up spool (56), floss-connected to respective subcapstans, dispense and take up floss. A floss-engaging portion of each subcapstan differs from the other in diameter to result in a net transfer of the floss from one spool to the other. Means for reciprocating the tines moves the span up and down. A pair of stationary shield tines (16) shield the user's teeth from the reciprocating tines. A second embodiment (90) includes an astable pulse generator (106) that generates a train of pulses of alternately reversing electric charge. Pulses of one charge are of longer duration than those of the other charge. A reversible DC motor (104) is drivingly connected to floss dispensing and take-up spools (98, 100) which are floss-connected to each end, respectively, of a tine supported floss span (96). The motor, energized by the alternating pulses, alternately reverses direction to reciprocate the floss span. A net transfer of floss from one spool to the other results from the longer pulses. A third embodiment (116) includes two ultrasonic transducers (127, 128) connected to floss-supporting tines (118). The transducers are mounted at right angles to each other for reciprocating the tines and floss span up and down and side to side.

21 Claims, 4 Drawing Sheets

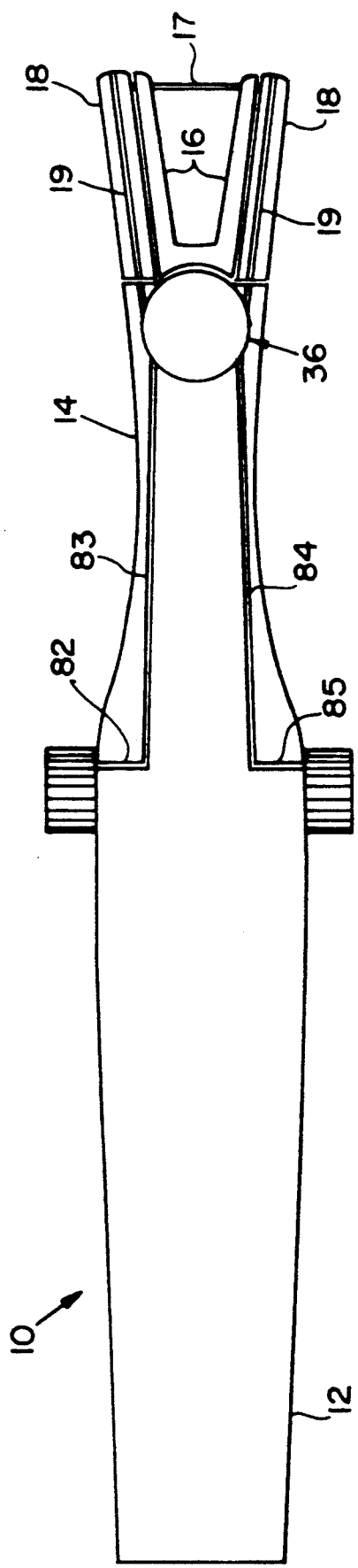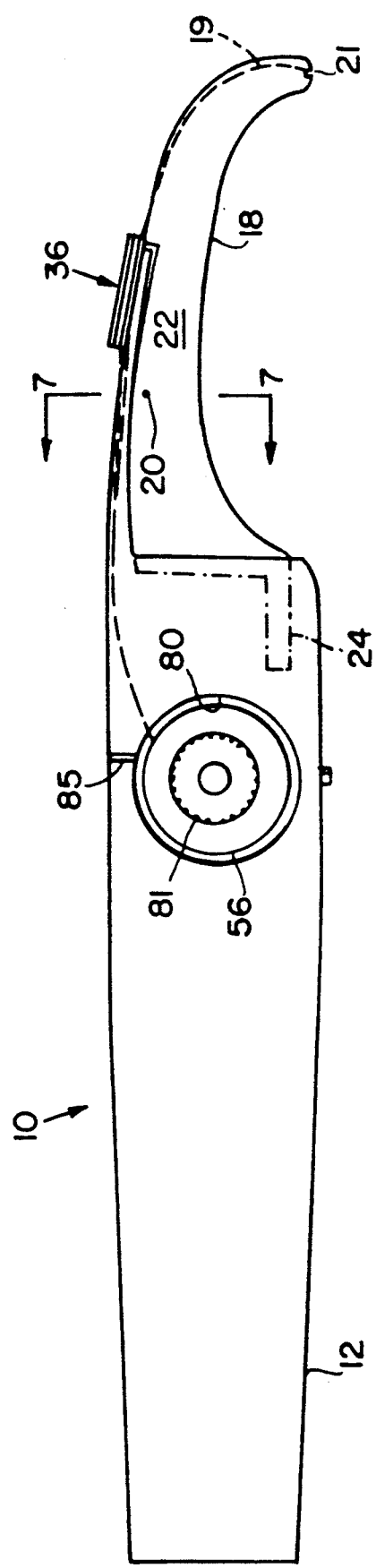

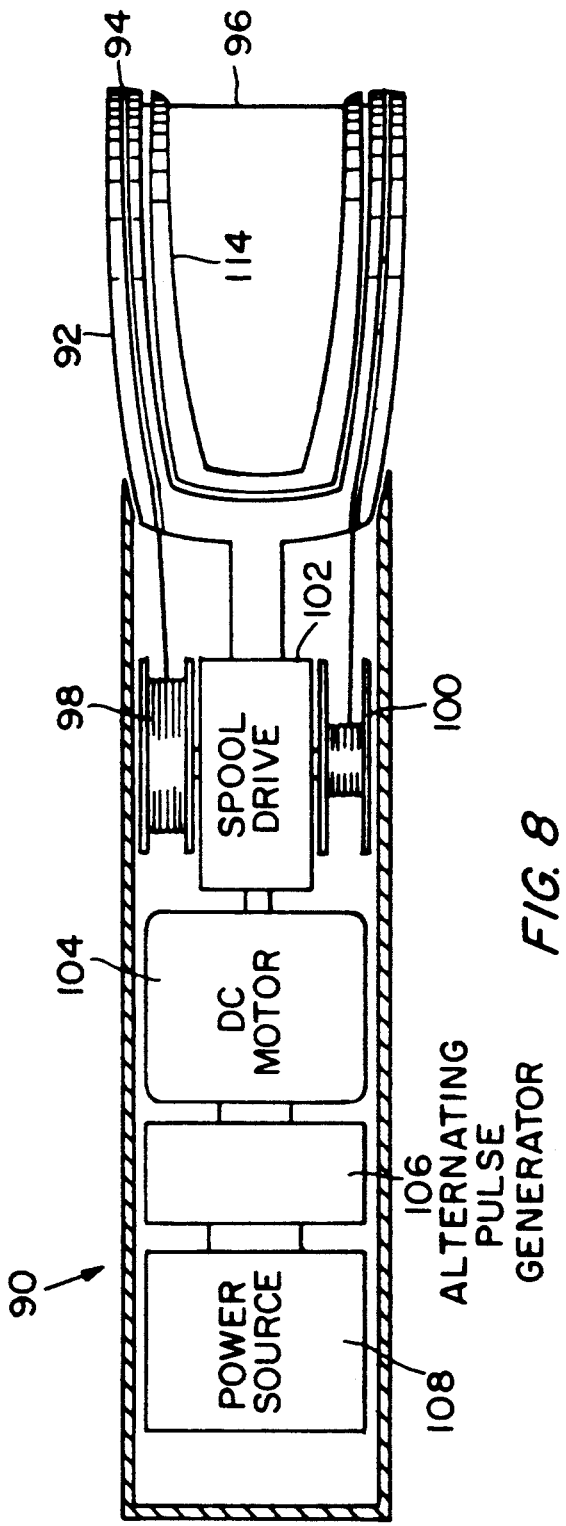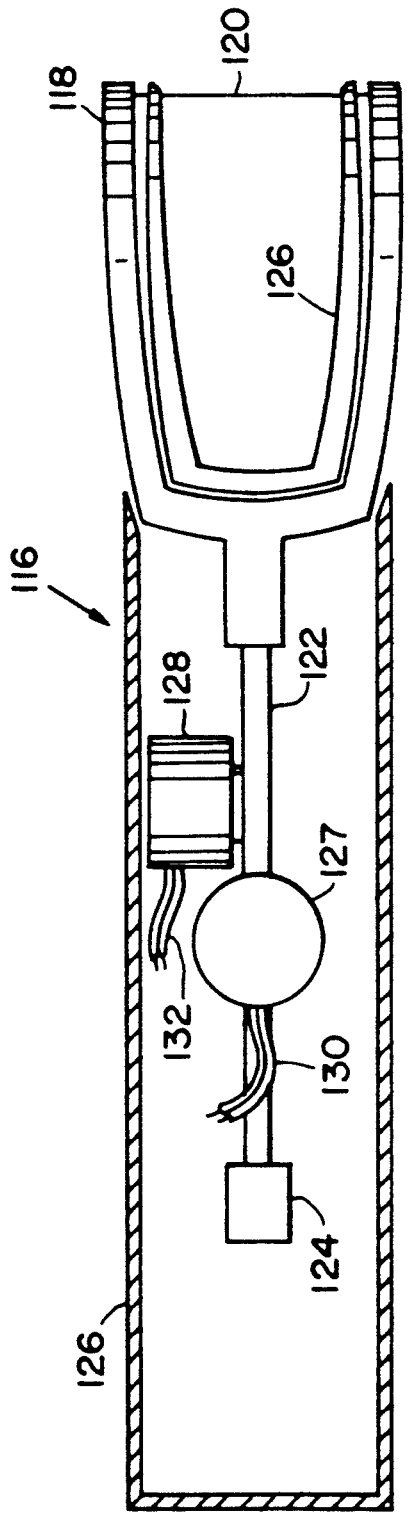

AUTOMATED DENTAL FLOSSER

TECHNICAL FIELD

This invention relates to dental flossing devices and more particularly to flossing devices having power driven means for reciprocating a floss span.

BACKGROUND

Most adults have some degree of gum disease. In an advanced form, the ailment accounts for about three quarters of lost teeth. Unhealthy gums can also lead to other health problems including serious infections.

Disease of the gums can be avoided by removal of plaque, especially from under the gum line. Brushing is not sufficient because it does not clean under the gum line between teeth. Consumer organizations have tested the available plaque removing products, including the high tech powered brushes. They report that the most important aspect of proper dental hygiene is flossing.

Proper flossing by hand, however, is an arduous and loathsome regimen. It requires dexterity and some degree of skill to properly manipulate the floss to clean all the interdental surfaces down to the attached gingiva. Dexterous people find flossing tedious and it is exceedingly difficult for the nondexterous. Consequently, an estimated 90 percent of adults have some degree of the disease in spite of efforts by their dentists to teach them how to floss.

An automated flosser is, therefore, needed to reduce the amount of tedious work, perseverance, and dexterity required for proper flossing. After building and testing a variety of powered models, it was found that a practical flosser must have four important features which are:

(1) Means for moving a floss span between teeth with lateral strokes in order to work the floss through the tight spot where adjacent teeth come in contact.

(2) Means for moving the span up and down which, after passing through the tight spot, operates with the lateral motions to remove plaque from interdental surfaces.

(3) Means for protecting the teeth and gums from being hammered by moving parts that reciprocate the floss span.

(4) Means for continuous replacement of the floss span.

Though several powered flossers have been patented, none have the desirable combination described above. The subject invention has the advantage of having the complete combination of above-mentioned features operating in concert. Other advantages will become apparent from consideration of the drawings and ensuing description.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale and in which drawings:

FIG. 1 is a top view of an automated flosser constructed in accordance with the invention;

FIG. 2 is a side view in elevation of the flosser of FIG. 1;

FIG. 8 is a top view, partly diagrammatic, of a second flosser embodiment showing means for reciprocating a floss span;

FIG. 10 is a top view, partly diagrammatic, of a third flosser embodiment showing another means for reciprocating a floss span.

DETAILED DESCRIPTION

A preferred embodiment of an automated flosser embodying the principles of the subject invention is shown in FIGS. 1-7. In FIG. 1, the flosser 10 comprises a hollow housing 12 having a square cross-section medially and tapers to a round cross-section posteriorly. Extending anteriorly of the housing is an elongated cantilever 14. Extending anteriorly of the cantilever is a pair of shield tines 16.

Figure 3:
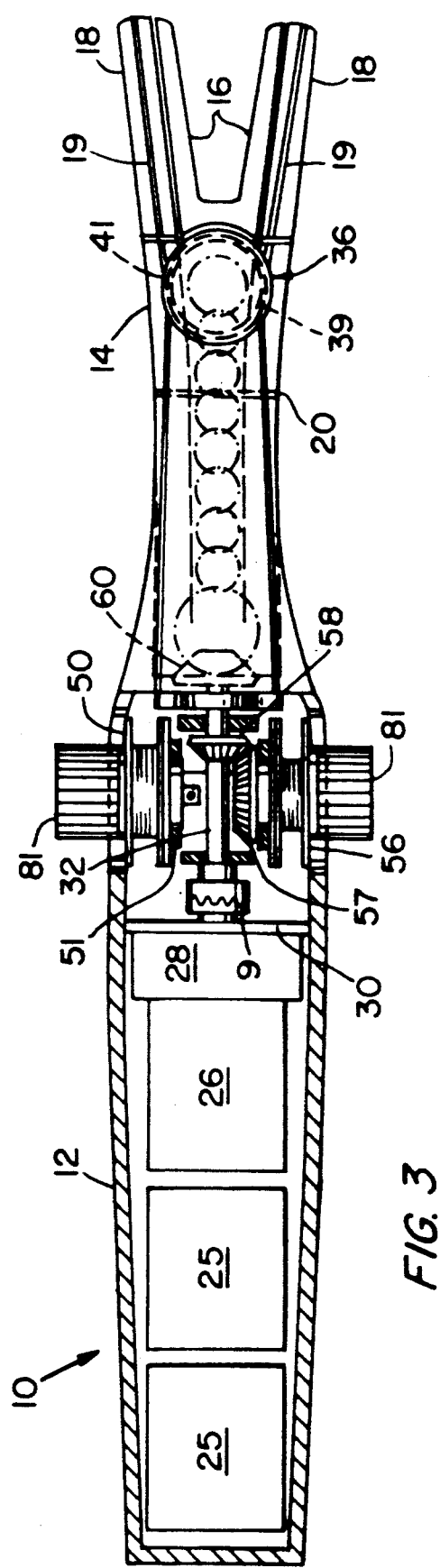
FIG. 3 is a top view, partly in section taken horizontally along the longitudinal axis of the flosser of FIG. 2.
Figure 4:
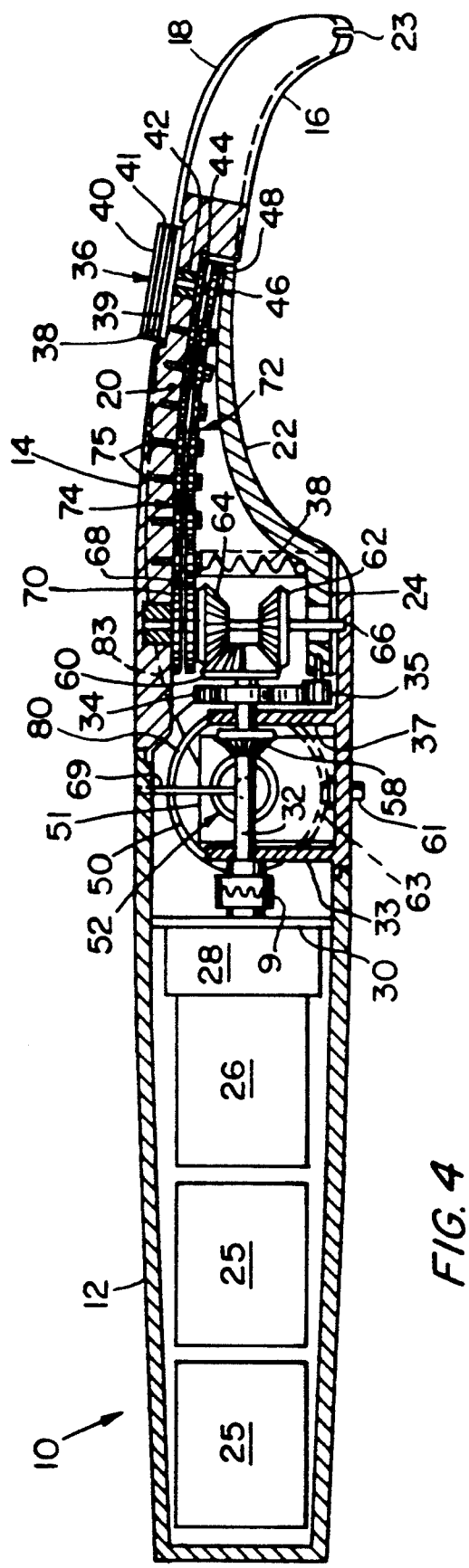
FIG. 4 is cross-sectional view taken vertically along the longitudinal axis of the flosser of FIG. 2.
Figure 7:
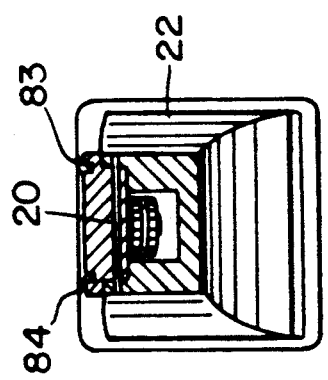
FIG. 7 is a cross-sectional view taken along the line 7—7 of FIG. 2.
Figure 6:
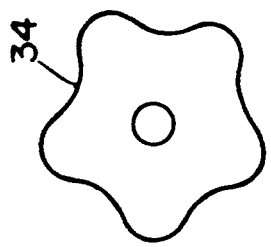
FIG. 6 is an expanded side elevation view of a multi-lobed cam.
Figure 5:
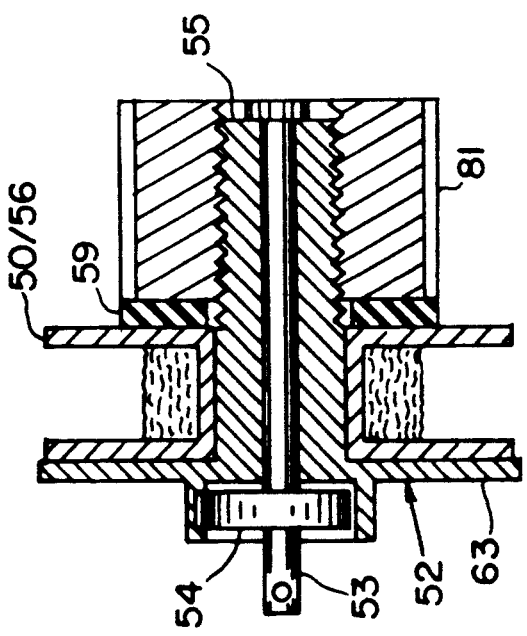
FIG. 5 is an expanded cross-sectional view of a spring driven floss spool mounted on a slip clutch.

Positioned laterally of the shield tines is a pair of reciprocating tines 18 which extend anteriorly from a lever 22 (FIGS. 2, 4 and 7). Lever 22 has a U-shaped cross-section (see FIG. 7). Tines 18 and lever 22 form a one-piece unit pivotally connected to the cantilever by a pin 20 (FIGS. 2, 3, 4 and 7). A posterior end portion 24 (FIGS. 2 and 4) of the lever is received through an opening in an end portion of housing 12 to reciprocate up and down therein.

Means for reciprocating lever 22, and thereby reciprocating tines 18, comprises a motor 26 (FIGS. 3 and 4) having conventional speed reduction means 28. Rechargeable batteries 25 power the motor by way of a conventional wiring circuit (not shown). A partition 30 sealed by conventional means (not shown) prevents water from entering the portion of housing 12 that houses the electrical components.

A multi-jawed coupling 9 drivingly connects the motor and speed reduction means to a drive shaft 32 (FIG. 4). The drive shaft is rotatably supported by bearing supports 33, 37.

Fixed to an anterior portion of the drive shaft is a multi-lobed cam 34 (FIGS. 4 and 6) which engages a cam follower 35. The follower 35 comprises a rotor rotatably supported on a pin inserted into end portion 24 of lever 22.

Also attached to lever portion 24 is one end of a tension spring 38 (FIG. 4). The opposite end of the spring is attached to the cantilever 14 under tension so that the reciprocating tines are spring urged downward. When the motor drives cam 34 to rotate, each lobe of the cam moves lever portion 24 downward, thus moving the reciprocating tines upward. After each cam lobe passes over the follower, the spring returns the reciprocating tines downward. In concert, the actions reciprocate the tines up and down.

Each reciprocating tine includes a floss guide groove 19 FIGS. 1, 2 and 3) which leads to a notch 21 (FIG. 2) in the distal end of the tine. The groove and notch provide floss guide means for guiding the transfer of dental floss from one reciprocating tine to the other. This forms a floss span 17 (FIG. 1) between the tines. A distal end portion of each shield tine 16 includes a vertical slot 23 (FIG. 4) for allowing span 17 to pass through the shield tines.

A system for reciprocating span 17 longitudinally of the span includes a double-acting capstan 36 comprising a first subcapstan 38 (FIG. 4) and a second subcapstan 40.

Subcapstan 38 comprises a disk coaxially fixed to an upper end portion of a hollow shaft 42 received in a bore through the hub of the disk. A mid portion of shaft 42 is rotatably supported in a vertical bore through an anterior portion of cantilever 14. Coaxially fixed to a lower end portion of shaft 42 is an upper driven gear 44. Subcapstan 38 includes a rim having an endless grooved portion 39 for engaging floss connected to one end of floss span 17.

Subcapstan 40 comprises a disk coaxially fixed to an upper end portion of a slender shaft 46 which is rotatably supported within hollow shaft 42. Coaxially fixed to a lower end portion of shaft 46 is a lower driven gear 48. As shown and described, the first and second subcapstans are mounted on separate shafts having a common axis. The subcapstans can be driven to rotate independently of each other by way of the driven gears 44, 48. Subcapstan 40 includes a rim having an endless grooved portion 41 for engaging floss connected to an opposite end of floss span 17.

As indicated in FIG. 3, each grooved portion 39, 41 has a diameter which differs from the other; grooved portion 41 having the greater diameter.

Means for driving the subcapstans comprises a rotatable driver or beveled sector gear 60 (best seen in FIG. 4) having a radial driving sector. The driving sector is a 180 degree sector of teeth which alternately engages a first beveled gear 62 and a second bevel gear 64 when gear 60 is driven. As result, the first and second gears are driven alternately in opposite directions. Gear 60 is driven by being coaxially fixed to the anterior end of drive shaft 32.

Gear 62 is coaxially fixed to a rotatably mounted shaft 66 which coaxially passes through gear 64, and through a third gear 68 and fourth gear 70. Gear 64 interfaces and is fixed to gear 68 wherein both rotate when gear 64 is driven. However, gears 64 and 68 are not fixed to shaft 66, but merely slip around the shaft when rotating. Gear 70 is fixed to shaft 66 and therefore rotates when gear 62 is driven.

Gear 68 is drivingly connected to gear 46 by means of a lower gear train 72. Similarly, gear 70 is drivingly connected to gear 44 by means of an upper gear train 74. All the gears of both trains are of the same size. Each gear of the upper train is supported along with a gear of the lower train on a nonthreaded portion of a pin or screw shaft 75. Each shaft 75 is inserted or screwed into the underside of cantilever 14 wherein the upper and lower gears of the trains slip around the shafts to rotate. Hence the upper train gears can rotate independently of the lower train gears and vice versa. The gear trains are housed within the U-shaped hollow of lever 22.

From the figures and the above description, it can be understood that the driving sector of the driver (gear 60) is alternately connected (by a gear train) with each subcapstan and alternately drives each subcapstan to rotate when gear 60 is motor driven.

In an alternative drive system (not shown), a toothless driver having a high friction driving sector could drive toothless high friction wheels instead of gears in an arrangement similar to that described above.

In another alternative drive system (not shown) a toothless sector driver could be positioned between two subcapstans so as to be alternately engaged with each subcapstan as the driver rotates. Hence, the subcapstans could be driven by direct friction contact with the driver. This simplified arrangement would obviate all the intervening gears.

Mounted within housing 12 is a floss dispensing spool 50 (FIG. 3 and 4) containing wound dental floss. A floss take-up spool 56 (FIGS. 2 and 3) is also mounted within housing 12. Each spool is supported to rotate on a respective slip clutch 52 (FIG. 4 and 5) partially housed in a hollow hub of the spool.

As shown in FIGS. 3 and 4, an inner end portion of each clutch is rotatably supported in an aperture in a respective vertical support 51. Each support 51 is fixedly attached to the floor of housing 12, thereby supporting a clutch and spool.

Each clutch includes an internally threaded knob 81 (FIG. 5) mated to a threaded portion of a sleeve 55. Extending radially from the sleeve is a flange 63 which interfaces with a floss spool (50 or 56) rotatably supported on the sleeve. A rubber washer 59 is compressed between the knob and spool to resist slip rotation of the spool about the sleeve. However, a sufficient amount of slip torque on the spool can overcome the resistance wherein the spool will slip around sleeve 55.

Each clutch houses a torsion spring 54 surrounding a shaft 53. The spring has an inner end connected to shaft 53 and an outer end connected to sleeve 55 in which the shaft is rotatably supported. The slip torque required to cause the spool to slip is slightly greater than the torque required to wind the spring. When floss, engaged by a rotating subcapstan, is drawn from a spool, the spool rotates in a floss unwinding direction thereby winding spring 54. When there is slack in the floss strand, the spring rapidly winds the slack onto the spool by driving the spool in a winding direction. Hence, when floss-connected to a subcapstan, each spool cyclically gives and takes floss as the subcapstan alternately reverses direction.

Referring to FIG. 3, coaxially fixed to the clutch shaft associated with spool 56 is a bevel gear 57. A pinion bevel gear 58 is coaxially fixed to shaft 32 and is drivingly engaged with gear 57. When shaft 32 is driven, spool 56 winds used floss.

When take-up spool 56 is floss-connected to subcapstan 40, the alternately reversing subcapstan cyclically gives and takes floss to and from the spool. However, the take-up spool winds more than it unwinds do to the greater floss engaging diameter of subcapstan 40 (relative to that of subcapstan 38). This results in a net transfer of floss from the dispensing spool to the take-up spool.

The cyclic give-and-take action also occurs between subcapstan 38 and dispensing spool 50 when they are floss-connected and operating. The clutch shaft associated with the dispensing spool is prevented from rotating by a pin 69 passing through housing 12 and through an aperture in the shaft. After spring 54 is fully wound, spool 50 slips opposite the direction urged by the spring as more floss is drawn.

The slip clutches also allow the flosser to be removed from the user's mouth in the event that floss gets caught under an overhanging tooth filling. In that situation, either spool can slip to yield floss Which can then be cut and laterally slipped out from between teeth.

OPERATION OF THE FLOSSER

A floss circuit is arranged by routing floss, from the dispensing spool, through the guide grooves of the flosser and attaching the strand to the take-up spool. Slots 82, 85 (FIG. 1 and 2) through housing 12 allow floss passage between the interior and exterior of the housing. Thus, floss from the dispensing spool passes through slot 82, runs along guide groove 83 (FIG. 1) and encircles the groove of the first subcapstan. The floss then passes through guide groove 19 and notch 21, of the nearest reciprocating tine, and spans across to the notch and groove of the opposite tine thereby forming span 17. Then the floss encircles the groove of the second subcapstan and travels along guide groove 84 to pass through slot 85. Attachment of the floss to the take-up spool completes the circuit.

When the motor is energized, the side-to-side movement of the operating floss span easily works its way through the tight spot or contact point between adjacent teeth. After passing through the tight spot, the faster up and down motion operates in concert With the side-to-side movement for efficient plaque removal. Span 17 is continuously replaced with clean floss as the used floss is taken up by the take-up spool.

After unscrewing the knobs 81, spools 50, 56 can be removed from housing 12 by way of an annular aperture 80 (FIGS. 2 and 4) in each opposing sidewall of the housing. After replacing a spool, a user can press a grip button 61 (FIG. 4) to prevent sleeve 55 from rotating so that the user can retighten knob 81. The grip button 61 is housed in a cavity in the housing 12 and support 51 and the button makes friction contact with flange 63.

SECOND EMBODIMENT

FIG. 8 shows an alternative flosser embodiment 90. Included is a fork 92 having grooved guide means 94 in each tine for guiding the transfer of dental floss from one tine to the other. The floss forms a longitudinally movable floss span 96 between the tines.

A rotatably supported first spool or floss dispensing spool 98 is floss-connected to an end of span 96. A rotatably supported second spool or take-up spool 100 is floss-connected to an opposite end of the span.

A conventional spool drive 102, having speed reduction gears, drivingly connects a reversible DC motor 104 to both spools. Each spool is driven in a winding direction with each direction that the motor shaft turns, respectively. That is, one spool winds when the motor shaft rotates in one direction and the other spool winds when the motor shaft rotates in the opposite direction.

Each spool is mounted on a conventional one-way slip clutch (not shown) for allowing each spool to slip in an unwinding direction when giving up floss to the driven spool.

Figure 9:
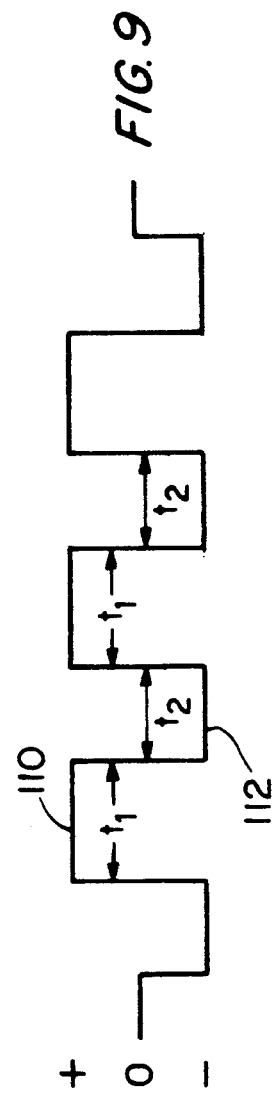
FIG. 9 is a diagram of a pulse train generated by an astable alternating pulse generator.

A conventional astable alternating pulse generator 106 is electrically connected to motor 104. A conventional electric power source 108, such as a battery, is connected to supply the generator. The generator produces a train of pulses which alternate in electrical charge as indicated in FIG. 9. The pulses energize the motor to alternately reverse direction thereby driving the spools in alternating directions. This causes the floss span to reciprocate longitudinally to work through the tight contact points between teeth.

Being of an astable design, the generator 106 produces pulses of one charge to be of longer duration than the pulses of the opposite charge. As indicated in FIG. 9, the positive pulses 110 have a slightly longer time duration than the negative pulses 112 wherein t1 is greater than t2. The running time for each direction that the floss is driven is the time duration of a pulse. The motor and generator are electrically connected such that the take-up spool is driven in a winding direction by the longer pulses to result in a net transfer of floss from the dispensing spool to the take-up spool.

Electronic details of the astable pulse generator are not shown since the pulse train of FIG. 9 can produced by conventional methods known in the electronic arts. A 555 or 556 timer IC (not shown) may be used in an astable pulse generator to generate pulses of proper time duration.

Fork 92 can be mounted and driven to reciprocate up and down by means described herein for the preferred or first embodiment. As in the first embodiment, a stationary shield fork 114 (FIG. 8) is included for shielding teeth and gums. Though other features of the first embodiment can also be included, they are left out of FIG. 8 for clarity.

THIRD EMBODIMENT

FIG. 10 shows a third flosser embodiment 116 having a fork 118 supporting a floss span 120. The fork extends from a lever 122 having an end portion fitted into a rubber mounting block 124. The block is fixed to the housing 126 of the flosser. As mounted, the fork is movable due to the resilient support of block 124. A stationary shield fork 126 is provided on inner lateral sides of the movable fork 118.

Mounted to the lever is a first transducer 127 directed for vibrating the fork up and down along with floss span 120. A second transducer 128 is mounted to the lever at a position ninety degrees round the lever axis relative to the first transducer. Hence, transducer 128 vibrates the fork 110 laterally or side to side.

An electric power source (not shown) powers the transducers by way of wires 130, 132.

Means (not shown) may be included for continuously replacing the floss span as described and illustrated for the first or second embodiments.

While the above description contains many specificities, these should not be construed as limitations on the scope of the invention, but rather as an exemplifications of preferred embodiments. Those skilled in the art will envision other possible variations that are within its scope. Accordingly, the scope of the invention should be determined not by the embodiments illustrated, but by the appended claims and their legal equivalents.

What is claimed is:

1. An automated flosser comprising:
a housing;
a pair of spaced tines supported on the housing, the tines having guide means for guiding the transfer of dental floss from one tine to the other tine to form a longitudinally movable floss span between the tines;
a double-acting capstan having two subcapstans for connecting to each end, respectively, of the floss span in order to drive the span to move longitudinally, the subcapstans being supported to rotate relative to each other;

capstan drive means for driving the subcapstans to rotate in alternating directions to reciprocate the span; and floss changing means for replacing the floss span, the changing means having means for supporting a replaceable floss dispensing spool for being floss-connected to the capstan thereby drawing floss from the spool and replacing the span.

2. The flosser as defined in claim 1, further comprising:

one of said subcapstans having a diameter greater than the other subcapstan diameter; and a take-up spool for being floss-connected to the subcapstan having the greater diameter thereby resulting in net transfer of floss to the take-up spool.

3. The flosser as defined in claim 1, further comprising:

spool drive means for urging the spool to rotate in a floss winding direction so that the spool can cyclically give-and-take floss.

4. The flosser as defined in claim 3, wherein the spool drive means comprises a spring connected to the spool for rotating the spool in a floss winding direction.

5. The flosser as defined in claim 3, further comprising slip means for allowing the spool to slip opposite the rotational direction urged by the spool drive means as floss is drawn from the spool.

6. The flosser as defined in claim 5, wherein the slip means comprises a slip clutch connected to the spool.

7. The flosser as defined in claim 1, wherein the capstan drive means is arranged for driving the subcapstans to rotate coaxially in opposite directions relative to each other.

8. An automated flosser comprising:

a housing;

a pair of spaced tines supported on the housing, the tines having guide means for guiding the transfer of dental floss from one tine to the other tine to form a longitudinally movable floss span between the tines;

first and second subcapstans for connecting to each end, respectively, of the floss span in order to drive the span to move longitudinally, the subcapstans being supported to rotate relative to each other;

subcapstan drive means for driving the subcapstans alternately in order to reciprocate the span; and floss changing means for replacing the floss span, the changing means having means for supporting a replaceable floss dispensing spool for being floss-connected to the subcapstans thereby drawing floss from the spool and replacing the span.

9. The flosser as defined in claim 8, wherein the two subcapstans are supported to rotate about a common axis.

10. The flosser as defined in claim 9, wherein the subcapstan drive means is arranged for driving the subcapstans to rotate in opposite directions relative to each other.

11. The flosser as defined in claim 8, wherein the subcapstan drive means comprises:

a rotatably supported driver having a radial driving sector alternately connectable with each subcapstan for alternately driving each subcapstan as the driver rotates such that the subcapstans are driven one at a time; and means for driving the driver to rotate.

12. The flosser as defined in claim 8, further comprising:

spool drive means for urging the spool to rotate in a floss winding direction so that the spool can cyclically give-and-take floss.

13. The flosser as defined in claim 12, wherein the spool drive means comprises a spring connected to the spool for rotating the spool in a floss winding direction.

14. The flosser as defined in claim 12, further comprising slip means for allowing the spool to slip opposite the rotational direction urged by the spool drive means as floss is drawn from the spool.

15. The flosser as defined in claim 14, wherein the slip means comprises a slip clutch connected to the spool.

16. The flosser as defined in claim 12, further comprising:

one of said subcapstans having a diameter greater than the other subcapstan diameter; and a floss take-up spool rotatably supported for being floss-connected to the subcapstan having the greater diameter so that a net transfer of floss to the take-up spool results.

17. An automated flosser comprising:

a housing;

a pair of tines supported on the housing, the tines being spaced for receiving teeth to be cleaned therebetween, the tines having guide means for guiding the transfer of dental floss from one tine to the other tine to form a longitudinally movable floss span between the tines;

means for rotatably supporting first and second floss spools for being floss-connected to respective ends of the floss span;

a reversible motor connected for driving the spools to rotate thereby moving the span; and an alternating pulse generator electrically connected to the motor, the generator for generating pulses alternating in electrical charge so that the motor alternates rotational directions thereby reciprocating the floss span.

18. The automated flosser as defined in claim 17, wherein the pulse generator is astable for causing the pulses of one charge to be of longer duration than the pulses of the opposite charge to result in net transfer of floss from one spool to the other.

19. An automated flosser comprising:

a housing;

a fork movably supported on the housing, the fork having a pair of tines spaced for receiving teeth to be cleaned therebetween, the tines having means for supporting a floss span between the tines; and a transducer connected to the fork for oscillating the floss span in order to clean teeth, the transducer being directed to vibrate the fork in an essentially laterally side-to-side direction thereby oscillating the floss span longitudinally.

20. The flosser as defined in claim 19, further comprising another transducer connected to the fork and directed transversely relative to the other transducer for oscillating the floss span in another direction.

21. An automated flosser comprising:

a housing;

a pair of spaced tines supported on the housing, the tines having means for supporting a floss span between the tines;

a first transducer connected to the tines for oscillating the floss span in order to clean teeth; and a second transducer positioned transversely relative to the first transducer for oscillating the floss span in another direction.

* * * * *